United States Patent [19]

Marchand et al.

[11] Patent Number: 5,089,572
[45] Date of Patent: Feb. 18, 1992

[54] BLANKING PROCESS FOR REACTION MIXTURE

[75] Inventors: Gary R. Marchand; Joseph G. Schell, Jr.; Brian W. Walther, all of Baton Rouge, La.; Corwin J. Bredeweg, Midland, Mich.

[73] Assignee: The Dow Chemical Company, Midland, Mich.

[21] Appl. No.: 395,176

[22] Filed: Aug. 18, 1989

Related U.S. Application Data

[63] Continuation-in-part of Ser. No. 157,761, Feb. 19, 1988, abandoned.

[51] Int. Cl.$^5$ .............................................. C07B 63/00
[52] U.S. Cl. ...................................... 526/77; 526/173; 526/912; 260/665 R; 260/701
[58] Field of Search ................. 526/77, 173, 60; 585/855; 260/665 R, 701

[56] References Cited

U.S. PATENT DOCUMENTS

| | | | |
|---|---|---|---|
| 3,743,629 | 7/1973 | Fraga | 526/60 |
| 4,172,190 | 10/1979 | Tung et al. | 526/173 |
| 4,201,729 | 5/1980 | Tung et al. | 526/173 X |
| 4,883,846 | 11/1989 | Moore et al. | 526/77 |
| 4,960,842 | 10/1990 | Lo et al. | 526/175 |

OTHER PUBLICATIONS

Wenger et al., Makromol. Chemie 45, 1-11 (1961).

*Primary Examiner*—Fred Teskin

[57] ABSTRACT

A process for blanking a reaction mixture utilizing as a blanking agent a difunctional lithium composition.

11 Claims, No Drawings

BLANKING PROCESS FOR REACTION MIXTURE

CROSS-REFERENCE TO RELATED APPLICATION

This is a continuation in part, of application Ser. No. 157,761 filed Feb. 19, 1988, now abandoned.

BACKGROUND OF THE INVENTION

The present invention relates to a process for removing contaminants from a reaction mixture such as a polymerization mixture, a Friedel Crafts alkylation mixture, etc.

Because of the presence of small amounts of water, alcohols or other proton donating species that interfere with many desirable chemical reactions, it may be necessary to blank, that is to remove, such contaminants. The removal of water from chemical reagents or a chemical reaction system is very important in many reactions involving inorganic and organometallic reagents such as Grignard reagents, alkyllithium reagents, metal halides, and metal hydrides. This procedure is especially desirable in polymerization reactions such as anionic and Ziegler Natta polymerizations. Reaction mixtures employed in anionic polymerizations are particularly sensitive to contamination and the components thereof should be blanked prior to addition of a calculated amount of an anionic polymerization initiator in order to achieve an accurately reproducible molecular weight product. Because the levels of contaminates may vary from batch to batch, it is particularly critical in the preparation of polymers prepared by batch polymerizations to eliminate interfering quantities of contaminates in order that the actual ratio of active polymerization initiator to monomer be accurately known. Only in this manner may the molecular weight of the resulting polymer be accurately reproduced from batch to batch.

Techniques for determining the correct amount of blanking reagent to be added to a reaction mixture are generally limited to the following procedures. A small sample of the mixture may be remotely analyzed utilizing gas chromatographic, or other suitable analytical technique, to determine the amount of undesirable contaminates present therein. From the analysis, it is thereafter possible to determine the correct amount of blanking agent that should be added to the mixture. Processes such as the aforementioned have the following deficiencies. First, the removing of a sample may itself introduce additional contaminates into the sample. Additionally, a sample volume ratio must be employed in the calculation of the amount of blanking agent to add to the reaction mixture, thereby introducing a source of error. Finally, interim variation in the primary solution may develop while the analysis and calculation are being performed. That is, the blanking is not performed in "real time".

An additional technique for determining the correct amount of blanking agent to be added utilizes titration of the entire reaction mixture utilizing a suitable reagent under conditions such that onset of reaction with the desirable ingredients in the mixture is detected. One version of this technique involving anionic polymerization requires the presence of a monomer in the polymerizable mixture capable of forming a colored anionic species. A typical example is a vinyl aromatic monomer such as styrene. The blanking reagent may be an alkyl lithium, generally butyllithium. The formation of a living polymer does not occur until after the substantial elimination of all contaminating species. When this point is reached, formation of the brightly colored polymeric anion clearly indicates the onset of polymerization and hence the complete consumption of all contaminating species. Unfortunately, the above indication of the onset of polymerization is only applicable to those monomer species capable of forming brightly colored anions. Diene monomers, particularly conjugated diene monomers, generally fail to form such brightly colored anions. Moreover, depending on the position in the electromagnetic spectrum where a colored species absorbs and the intensity of that absorption (extinction coefficient) a colored end point indicator may be of little value. Absorption must occur in an area of the spectrum that is unaffected by other colored species in the reaction mixture and be of sufficient intensity that extremely small quantities thereof are detectable. Desirably, the molar extinction coefficient of the colored species to be detected should be greater than about 10,000 l/mole-cm preferably greater than about 30,000 l/mole-cm.

In anionic polymerization mixtures it is known to use lower alkyl lithium initiators as blanking agents. A particular deficiency with the use of such alkyl lithium blanking agents is the relatively fast reaction of such compounds with monomers to form polymeric and oligomeric species. Such highly reactive blanking agents may form significant amounts of such species before removing the contaminants via the desired blanking reaction.

It would be desirable if there were provided an improved blanking technique.

It would further be desirable to provide a blanking process for removing contaminates from reaction mixtures that is not dependent on the formation of colored reaction products such as living polymer anions in an anionically polymerizable mixture.

It would further be desirable if there were provided a blanking process for an anionic polymerization mixture wherein the consumption of contaminating species is indicated by a process other than the onset of polymerization.

Lastly, it would be desirable if there were provided a process for the blanking of batch polymerization mixtures that is conducted in real time utilizing a reagent that reacts rapidly with the impurities of the reaction mixture and less rapidly with the monomers to be polymerized.

SUMMARY OF THE INVENTION

According to the present invention there is now provided a process for blanking reaction mixtures in order to remove proton donating impurities occurring therein wherein the reagent employed as the blanking agent comprises a compound selected from the group consisting of compounds corresponding to the formula:

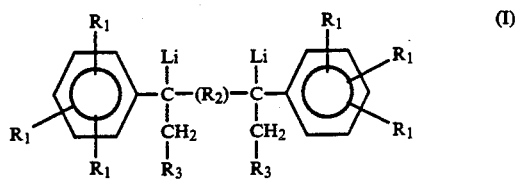

wherein:

$R_1$ is independently each occurrence hydrogen or an inert radical having from 0 to 16, preferably 1 to 6 carbon atoms;

$R_2$ is a divalent organic radical having at least 6 carbon atoms, $R_2$ having at least one aromatic ring and the aromatic ring being directly attached to a carbon which is attached to an aromatic ring of the above formula: and $R_3$ is selected from the group consisting of alkyl, cycloalkyl, and aromatic radicals containing from 1 to 20 carbon atoms.

In the utilization of the aforementioned highly colored blanking agents, reaction with interfering contaminates prevents the general coloration of the reaction mixture. Thus, the onset of coloration indicates the destruction of substantially all interfering contaminates. In an anionic polymerization this endpoint indication is independent of living polymer anion formation. Moreover, because of the large extinction coefficient of the above blanking reagents and because the rate of anionic polymer initiation by the above blanking reagents is relatively slow, molecular weight or compositional variations in the resulting product due to the polymer initiation by the blanking agent in an anionic polymerization are considerably reduced. Thus the artisan may easily detect the end point of the blanking reaction and discontinue adding blanking agent before the formation of significant amounts of polymer anion results.

DETAILED DESCRIPTION OF THE INVENTION

The present blanking technique may be employed with any reaction mixture containing proton donating contaminants. Examples of such contaminants include water, alcohols, carboxylic acids, amines, thiols, etc. Additional components of the reaction mixture include inert diluents, polymerizable monomers, alkylation agents, alkylatable aromatic compounds, etc. Preferred components are anionic polymerization components. Preferred temperatures for the blanking process are from 20° C. to 90° C., most preferably from 30° C. to 60° C.

In particular regard to anionic polymerizations any anionically polymerizable monomer may be employed in the reaction mixture. Examples of such monomers include monovinylidene aromatic monomers such as styrene or α-methylstyrene and dienes, especially conjugated dienes, as well as mixtures thereof. Preferred conjugated diene monomers are butadiene and isoprene. Inert diluents include toluene, cyclohexane, hexane, etc.

While the individual components of the reaction mixture may be subjected to blanking, it is preferred to prepare a mixture comprising the desired reactants, e.g. monomers and any diluent or other desired ingredient and subjecting the entire mixture to the above described blanking process.

In a highly preferred embodiment of the present invention, the entire reaction mixture is blanked and the endpoint of the blanking process is determined by utilizing a photoelectronic detector means such as a photo detector adapted to determine the onset of color formation in the mixture. In a particularly preferred embodiment, the blanking process is conducted in the reactor wherein the ensuing reaction is to be conducted. The photoelectronic means for determining color formation in the reaction mixture may be connected to the reactor by use of a fiber optic, or other suitable signal transmitting means in operative communication with the reactor contents and the aforementioned photoelectronic detector means. In a most highly preferred embodiment of the present invention, an anionic polymerization process is disclosed wherein a difunctional initiator corresponding to the foregoing formula I is also employed.

Preferred blanking reagents for use according to the present invention are those compositions corresponding to the formula:

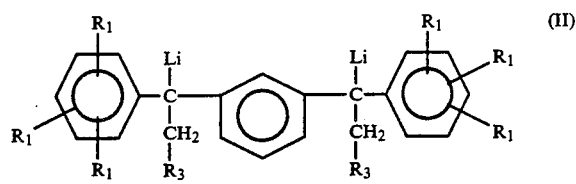

wherein $R_1$ is as previously defined and $R_3$ is $C_{1-6}$ alkyl.

Particularly preferred blanking reagents comprise 1,3-phenylene-bis(3-methyl-1-phenyl pentylidene)bis(lithium) and 1,3-phenylene bis(3-methyl-1-(4-methylphenyl)pentylidene)bis(lithium).

In order to obtain the highest accuracy in detecting the onset of color formation in the reaction mixture it is highly desirable to employ blanking reagents having an extinction coefficient of at least about 10,000 l/mole-cm, preferably at least about 30,000 l/mole-cm. The skilled artisan may readily determine the appropriate extinction coefficient from a qualitative standpoint by measuring the absorbency (the negative logarithm of transmittance) of a reference solution at a given wavelength. Then given the path length (L) in cm and concentration (C) in moles/liter of the solution the various parameters are interrelated by means of the formula:

ABSORBENCY = L × C × EXTINCTION COEFFICIENT

The above values are determined at wavelengths suitable for detection, preferably at wavelengths from about 300 nm to 650 nm. The use of such reagents results in facile determination of color formation by means of photoelectronic means.

It is to be further understood that a combination of blanking agents or techniques may be employed without departing from the scope of the present invention. In actual practice, a portion of the contaminating species may be first removed by addition of a small amount of a $C_{1-12}$ alkyl lithium compound or other strong base and final blanking accomplished according to the present invention. Alternatively, a mixture of the present blanking agent with a $C_{1-12}$ alkyl lithium compound may be employed as the blanking process.

Having described the invention the following examples are provided as further illustrative and are not to be construed as limiting.

EXAMPLE 1

A colorimeter adapted to record at 450 nm (Brinkman PC 701 colorimeter equipped with 450 nm interference filter and strip chart recorder) was connected to a 5 gallon (19 liter) standard laboratory reactor by means of a fiber optic probe of 2 cm length manufactured by Brinkman, Inc. The reactor was charged with 15 liters of purified toluene and 2.9 liters of isoprene. The colorimeter was adjusted to indicate zero absorbency.

A small supply vessel containing a 0.045 molar toluene solution of 1,3-phenylene bis(3-methyl-1-phenylpentylidene) bis-(lithium) (referred to hereinafter as blanking agent solution) and equipped with a metering device was attached to the reactor. The reactor was purged, charged with nitrogen and heated to 45° C. with stirring. The blanking agent solution was slowly added to the reactor. Initially, no change in measured absorbance occurred. After addition of 33 ml. of the blanking agent solution, transient absorbance peaks were recorded. After addition of 6 more ml of blanking agent solution (39 ml. total), a continuous absorption was recorded indicating no further reaction due to contaminants.

To initiate polymerization of the reaction mixture an additional quantity of 1,3-phenylene bis(3-methyl-1-phenylpentylidene) bis-(lithium) solution was added to the reactor vessel.

EXAMPLES 2-4

In Example 2, the same reactor configuration as in Example 1 was employed to prepare block copolymers of isoprene and styrene. The reactor was charged with 16.2 liters of purified cyclohexane. After the solvent was warmed to about 50° C., the blanking agent solution (a 0.0544 molar cyclohexane solution of 1,3-phenylene bis(3-methyl-1-phenylpentylidene) bis-(lithium)) was slowly metered into the reactor. A measurable absorbance was detected after the addition of 4.0 g of the blanking solution. After the above solvent blanking, 1.948 liters (1.3265 kg) of purified isoprene monomer were added to the reactor. The solution was warmed to 49° C. and more blanking solution was added. A measurable absorbance was detected after the addition of 54.5 g of blanking solution.

Polymerization was initiated by the addition of 14.2 ml of a 1.4M solution of sec-butyl lithium in cyclohexane. After 11 minutes, 0.258 liters of styrene monomer were added and allowed to react.

In Examples 3 and 4 the conditions of Example 2 are substantially repeated, but amounts of solvent, isoprene and styrene were altered thereby requiring the utilization of different amounts of blanking agent. The resulting polymers were analyzed by gel permeation chromatography (Waters 150C ALC/GPC using Nelson Model 2900 GPC software) to determine the number average molecular weight (Mn) of the product. No evidence of polymer initiation by the blanking agent was observed. For each polymer a targeted molecular weight (TMn) equal to the weight of monomer in grams divided by the moles of initiator used for polymerization only is provided. Also a theoretical molecular weight (ThMn) was also calculated which would have been the polymer molecular molecular weight if no blanking agent had been employed to remove impurities. The theoretical molecular weight may also be calculated according to the formula:

ThMn = Mn (M$_i$/M$_i$2Mb), where

Mn is the polymer's actual molecular weight,
M$_i$ is total moles of initiator added to the polymerization mixture, and
Mb is the moles of blanked impurities assuming that one mole of initiator reacts with 2 moles of impurities.

In Table 1 amounts of blanking agent utilized in the reaction, the targeted molecular weight, actual molecular weight as determined by gel permeation chromatography (Mn), theroetical molecular weight, and ratios of the various parameters are provided.

TABLE 1

| EX. | BLANKING AGENT (g) | TMn × 10$^{-3}$ | Mn × 10$^{-3}$ | Mn/ TMn | ThMn × 10$^{-3}$ | ThMn/ TMn |
|---|---|---|---|---|---|---|
| 2 | 58.4 | 79.5 | 80.6 | 1.014 | 101.7 | 1.278 |
| 3 | 12.0 | 65.0 | 65.4 | 1.006 | 69.2 | 1.064 |
| 4 | 10.5 | 65.0 | 65.9 | 1.014 | 69.2 | 1.065 |

It may be seen that the use of a blanking agent according to the present invention allows the obtainment of polymers in repeated batch polymerizations having exceptionally accurate reproduction of molecular weight. The variation in actual molecular weight from theoretical was a maximum of 1.4% utilizing the blanking agent whereas the maximum deviation without any blanking agent was 27.8%.

EXAMPLE 5

The reaction conditions of Example 1 were substantially repeated to prepare a block copolymer of styrene and isoprene starting first with the preparation of styrene homopolymer. The reactor was charged with 16.4 liters of purified cyclohexane and 0.268 liters of purified styrene monomer. After the solution was warmed to 59° C. a 0.0213M cyclohexane solution of 1,3-phenylene bis(3-methyl-1-phenylpentylidene) bis-(lithium) was slowly added to the reactor. A measurable absorbance was detected after addition of 28.5 ml. The polymerization was initiated by the addition of 17.3 ml of a 1.4M cyclohexane solution of sec-butyl lithium solution. After 31 minutes, 2.201 liters of isoprene monomer were added and allowed to react. The resulting polymer was recovered and analyzed as in Examples 2-4. Results are contained in Table 2.

TABLE 2

| EX. | BLANKING AGENT (g) | TMn × 10$^{-3}$ | Mn × 10$^{-3}$ | Mn/ TMn | ThMn × 10$^{-3}$ | ThMn/ TMn |
|---|---|---|---|---|---|---|
| 5 | 22.0 | 72.0 | 75.6 | 1.049 | 79.6 | 1.105 |

What is claimed is:

1. A process for blanking a reaction mixture comprising contaminating amounts of a proton donating reactive impurity in order to remove such proton donating reactive impurity but not to initiate reaction of the reaction mixture the steps of the process comprising: adding to the reaction mixture in a reactor wherein the ensuing reaction is to be conducted, at a temperature from 20° C. to 90° C., a sufficient amount to remove the proton donating impurity of a blanking agent comprising a composition corresponding to the formula:

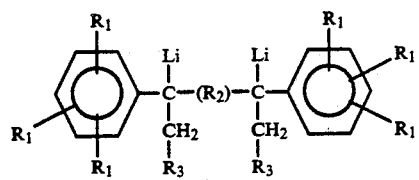

wherein:
R$_1$ is independently each occurrence hydrogen or an inert radical having from 0 to 16 carbon atoms;
R$_2$ is a divalent organic radical having at least 6 carbon atoms, R$_2$ having at least one aromatic ring and the aromatic ring being directly attached to a carbon which is attached to an aromatic ring of the above formula; and R₃ is selected from the group consisting of alkyl, cycloalkyl, and aromatic radicals containing from 1 to 20 carbon atoms.

2. A process according to claim 1 wherein the blanking agent comprises a compound corresponding to the formula:

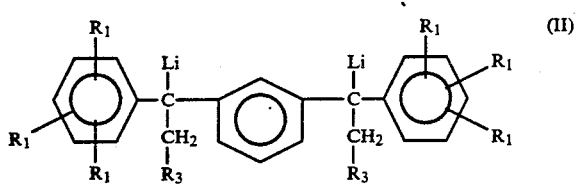
(II)

wherein R₁ is independently each occurrence hydrogen or an inert radical having from 0 to 16 carbon atoms; and R₃ is selected from the group consisting of alkyl, cycloalkyl, and aromatic radicals containing from 1 to 20 carbon atoms.

3. A process according to claim 2 wherein the blanking agent comprises 1,3-phenylene-bis(3-methyl-1-phenyl pentylidene)bis(lithium) or 1,3-phenylene-bis(3-methyl-1-(4-methyl phenyl) pentylidene)bis lithium.

4. A process according to claim 9 wherein the blanking agent has an extinction coefficient of at least 10,000 l/mole-cm at a detectable wavelength.

5. A process for blanking an anionic or Ziegler-Natta reaction mixture comprising contaminating amounts of a proton donating reactive impurity in order to remove such proton donating reactive impurity but not to initiate reaction of the reaction mixture the steps of the process comprising: adding to the reaction mixture in a reactor wherein the ensuing reaction is to be conducted, at a temperature from 20° C., to 90° C., a sufficient amount to remove the proton donating impurity of a blanking agent comprising a composition corresponding to the formula:

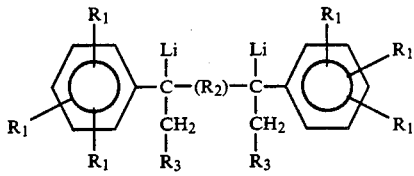

wherein:
R₁ is independently each occurrence hydrogen or an inert radical having from 0 to 16 carbon atoms;
R₂ is a divalent organic radical having at least 6 carbon atoms, R₂ having at least one aromatic ring and the aromatic ring being directly attached to a carbon which is attached to an aromatic ring of the above formula; and
R₃ is selected form the group consisting of alkyl, cycloalkyl, and aromatic radicals containing from 1 to 20 carbon atoms.

6. A process according to claim 1 or 5 wherein the reaction mixture is heated prior to addition of the blanking agent.

7. A process according to claim 6 wherein the reaction mixture is heated to a temperature of at least 45° C. prior to addition of the blanking agent.

8. A process according to claims 1 or 5 wherein the temperature is from 30° C. to 60° C.

9. A process according to claim 1 or 5 wherein the removal of the proton donating impurity is determined by a change in color of the reaction mixture.

10. A process according to claim 9 wherein the change in color is detected by a photoelectronic means.

11. A process according to claim 10 wherein the photoelectronic means comprises a fiber optic in operative communication with the reactor contents and a photodetector.

* * * * *